United States Patent [19]

Dahlberg et al.

[11] 4,056,672

[45] Nov. 1, 1977

[54] POLYMER PREPARED BY CYANHYDRIN METHOD

[75] Inventors: Alf-Göran Dahlberg, Nykvarn; Karl Gustav Högberg, Sodertalje; Sven Lindvall, Sodertalje; Thore Oskar Verner Rydh, Sodertalje, all of Sweden

[73] Assignee: Astra Lakemedel Aktiebolag, Sodertalje, Sweden

[21] Appl. No.: 576,152

[22] Filed: May 9, 1975

Related U.S. Application Data

[62] Division of Ser. No. 343,690, March 22, 1973, Pat. No. 3,928,581.

[51] Int. Cl.$^2$ .................. A61K 31/70; C07H 15/08
[52] U.S. Cl. .................. 536/1; 260/635 C; 424/78; 424/180; 536/4; 536/120
[58] Field of Search .................. 260/209 R; 424/180; 536/1, 120

[56] References Cited

U.S. PATENT DOCUMENTS

| | | | |
|---|---|---|---|
| 3,277,076 | 10/1966 | Yotsuzuka | 260/210 R |
| 3,369,014 | 2/1968 | Booth | 260/209 R |
| 3,370,056 | 2/1968 | Yotsuzuka et al. | 260/209 R |
| 3,433,751 | 3/1969 | Yotsuzuka et al. | 260/209 R |
| 3,442,888 | 5/1969 | Degginger et al. | 260/209 R |
| 3,477,802 | 11/1969 | Tesoro | 260/209 R |
| 3,535,307 | 10/1970 | Moss et al. | 260/209 R |
| 3,536,696 | 10/1970 | Alsop et al. | 260/209 D |
| 3,539,648 | 11/1970 | Orkin | 260/209 R |
| 3,829,412 | 8/1974 | Kunz | 260/209 R |
| 3,829,505 | 8/1974 | Herold | 260/209 R |
| 3,928,581 | 12/1975 | Dahlberg et al. | 536/121 |

*Primary Examiner*—Johnnie R. Brown
*Attorney, Agent, or Firm*—Brumbaugh, Graves, Donohue & Raymond

[57] ABSTRACT

The present invention relates to a process for preparing a polymer which is suitable for being administered parenterally from a saccharide, a polyhydric alcohol and a polymerization agent and to the polymer prepared therefrom. The invention relates also to an iron preparation suitable for parenteral — intramuscular and intravenous — injection, to a process for the preparation of the iron preparation, and to the use of the injectable iron preparations in human and veterinary medicine.

26 Claims, No Drawings

POLYMER PREPARED BY CYANHYDRIN METHOD

This is a division, of application Ser. No. 343,690 filed Mar. 22, 1973, now Pat. No. 3,928,581.

BACKGROUND OF THE INVENTION

In the treatment of iron deficiency in mammals, including man, iron may be administered orally with subsequent resorption via the alimentary canal, or parenterally by intravenous or intramuscular injection of a solution containing ion. In such solutions for parenteral administration, the iron must be present as ferric iron in a stabilized form in order to prevent gel formation and precipitation, for example, precipitation of ferric hydrate at physiological pH. The iron must also be present in such a form that no toxic side reactions, whether of a local or of a general type, occur when injecting dosages containing at least 100 mg. of iron. Solutions of salts or iron cannot be used for parenteral administration mainly because of their relatively high toxicity.

Various substances have previously been used as stabilizing agents in iron preparations for parenteral administration. In order to prevent precipitation of ferric hydrate by alkalization of an aqueous solution of a ferric salt solution, some kind of carbohydrate was heretofore early used as a stabilizing agent. Thus, one prior preparation for parenteral administration consisted essentially of an aqueous solution of a saccharated oxide of iron. However, in order to prevent precipitation of ferric hydroxide the pH of this iron preparation had to be alkaline, and parenteral administration of the preparation often led to undesirable side effects.

Other types of stabilizing agents previously used in preparations of iron for intramuscular injection are dextrins and dextrans. The use of dextrins and dextrans made it possible to prepare injection solutions with a physiological pH. However, preparations containing complex of low muscular weight dextran and iron having resulted in undesirable side effects, such as local pain and discoloration of the skin surrounding the site of the injection [Acta Medica Scandinavica Suppl. 342 T. Karlefors and A. Norden "Studies on iron-dextran complex (1968)"]. Dextrin, a degraded starch, contains reducing groups which may reduce some ferric iron in the iron preparation to ferrous iron. Presence of ferrous iron in the preparation is undesirable and a limiting factor which, because of its toxicity, may give rise to side effects when administered in high dosages.

Still another type of stabilizing agent used in the preparation of iron preparations for intramuscular administration is a combination of sorbitol, citric acid and dextrin (Canadian Pat. NO. 659,420). It was found that such a combination of sorbitol, citric acid and dextrin could be used to stabilze ferric iron so that an iron complex with an average molecular weight of about 5000 was obtained, whereas the previously used iron-dextran and iron-dextrin complexes had average molecular weights exceeding 150,000. The acute toxicity, LD 50, of this complex of iron for intraperitoneal administration to mice was about 50 mg per kg bodyweight, which toxicity, although higher than the toxicity of the iron-dextrin and iron-dextran preparations, still made possible administration of humans of dosages not exceeding 200 mg. of iron. Thus, a large number of injections to a single patient is necessary. The iron in this preparation, sold under the trade name "Jectofer", is present, in that form of particles of such small size that they are rapidly resorbed via both the lymphatic vessels and the blood vessels. The small size of the particles and the comparatively low average molecular weight also mean, however, that about 30% of the administered amount of iron is excreted via the kidneys. The remaining part of the administered iron is utilized to a very high degree at the hematopoiesis.

Thus, it would be advantageous to have a stabilizing agent which results in relatively low losses of administered iron via the kidneys and lower toxicity permitting administration to humans of single dosages containing more than 200 mg. of iron.

It would also be advantageous to avoid the presence of reducing groups in the dextrin which may convert part of the ferric iron to ferrous iron. As stated above, previously used stabilizing agents in iron preparations for intramuscular injection contain sugar or polymers of sugar, such as dextrin or dextran, which have a stabilizing effect on a ferric colloid at neutral pH. These previously used stabilizing agents commonly contain reducing groups which to some degree convert ferric iron in the injection solution to the ferrous iron. Ferrous iron is an undesired component in iron preparations for intramuscular injection due to its toxicity and may cause undesired side effects at administration of the solution to the patients. The amount of ferrous iron present in the injection solution may, due to its toxicity, constitute a limiting factor for the maximum dosage of iron which may be administered to the patient in each injection.

SUMMARY OF THE INVENTION

A main object of this invention is to provide an iron preparation for intramuscular administration which contains, as stabilizing agent, a new polymer which 1. has the capability to stabilize ferric iron at physiological pH,
2. causes an insignificant reduction of ferric iron to ferrous iron in an injection solution,
3. has the capability to yield a complex with ferric iron which has a low toxicity and after intramuscular injection is resorbed to a high degree from an intramuscular depot while only a minor part is excreted via the kidneys, and
4. has capability to yield a complex with ferric iron which has such toxicity that a dosage of more than 500 mg of iron may be administered to humans without serious side effects.

Thus, in accordance with this invention, these objects have been met with new iron preparations which is well resorbed and which has a low toxicity making administrations of unit dosages containing more than 500 mg iron possible without serious side effects. Although the main use of the new polymer used as stabilizing agent is in the preparation of iron preparations for intramuscular administration, other fields of use are apparent as described herebelow.

The present invention provides an iron preparation for intramuscular and intravenous injections which contains, as stabilizing agents, a physiologically innocuous, water swellable polymer which is a product prepared from a saccharide, and a polyhydric alcohol with a polymerizing agent selected from the group consisting of halogenated aliphatic alcohols transformable to epoxides in alkaline solution, the epoxides obtained thereby and mixtures thereof.

DETAILED DESCRIPTION OF THE INVENTION

The saccharides suitable for this invention are sucrose, trehalose, raffinose and mixtures thereof. The preferred compound is sucrose.

The term "polyhydic alcohol" as defined herein is at least one from a broad class of aliphatic alcohols containing 2 to 10 carbon atoms and 2 to 10 alcoholic hydroxyl groups. Because such alcohols which solely contain non-etherified groups, "polyhydric alcohol" as further defined herein include those which are partially etherified, i.e., one or more but not all of the alcoholic hydroxyl groups may be etherified. For instance, the hydroxyl groups may be etherified with $C_1$ to $C_5$ alkyl groups or with $C_1$ to $C_5$ hydroxylalkyl groups. One such suitable partially etherified alcohol, among others, is hydroxy propyl sorbitol.

Examples of polyhydric alcohols, among others, are glycerol and glycol with the structural formula:

```
    H2COH              H2C—OH
    |                  |
    H2C—OH             H2C—OH
    |
    H2C—CH glycerol           glycol
```

; tetritols, e.g., compounds with the structural formula:

```
    CH2OH              CH2OH
    |                  |
    HOCH               HCOH
    |                  |
    HCOH               HCOH
    |                  |
    CH2OH              CH2OH
```

; pentitols, e.g., compounds with the structural formula:

```
    CH2OH         CH2OH         CH2OH
    |             |             |
    HOCH          HCOH          HCOH
    |             |             |
    HCOH          HOCH          HCOH
    |             |             |
    CH2OH         HCOH          HCOH
                  |             |
                  CH2OH         CH2OH arabitol (lyxitol)  xylitol    ribitol (adonitol)
```

; hexitols, e.g., compounds with the structural formula:

```
  CH2OH      CH2OH      CH2OH      CH2OH
  |          |          |          |
  HCOH       HOCH       HOCH       HOCH
  |          |          |          |
  HOCH       HOCH       HOCH       HCOH
  |          |          |          |
  HCOH       HCOH       HOCH       HOCH
  |          |          |          |
  HCOH       HCOH       HCOH       HCOH
  |          |          |          |
  CH2OH      CH2OH      CH2OH      CH2OH sorbitol   mannitol    talitol    iditol
```

```
    CH2OH              CH2OH
    |                  |
    HCOH               HCOH
    |                  |
    HOCH               HCOH
    |                  |
    HOCH               HCOH
    |                  |
    HCOH               HCOH
    |                  |
    CH2OH              CH2OH galactitol           allitol
  (dulicitol)
```

; heptitols, e.g., compounds with the structural formula:

```
   CH2OH          CH2OH          CH2OH
   |              |              |
   HCOH           HOCH           HCOH
   |              |              |
   HCOH           HCOH           HOCH
   |              |              |
   HOCH           HOCH           HOCH
   |              |              |
   HCOH           HCOH           HCOH
   |              |              |
   HCOH           HCOH           HCOH
   |              |              |
   CH2OH          CH2OH          CH2OH glycero-gulo-  D-glycero-D-ido-  D-glycero-D-gala-
 heptitol       heptitol          heptitol
(α-Glucoheptitol) (D-β-Glycohepti- (Perseitol)
                    tol)         (α-Mannoheptitol)
```

```
  CH2OH       CH2OH       CH2OH       CH2OH
  |           |           |           |
  HOCH        HCOH        HOCH        HCOH
  |           |           |           |
  HOCH        HOCH        HCOH        HOCH
  |           |           |           |
  HCOH        HCOH        HOCH        HCOH
  |           |           |           |
  HCOH        HCOH        HOCH        HOCH
  |           |           |           |
  HCOH        HCOH        HCOH        HCOH
  |           |           |           |
  CH2OH       CH2OH       CH2OH       CH2OH

D-glycero-D-  D-glyceero-D-  D-glycero-L-  glycero-ido-
 manno         gluco          gluco         heptitol
 heptitol      heptitol       heptitol      (meso)
(Volemitol)   (β-Sedo-       (D-β-Gala-
(D-β-Manno-   heptitol)      heptitol)
 Heptitol)                   (D-α-Gulo-
(α-Sedo-                     heptitol)
 heptitol)
```

; octitols, nonitols and decitols, e.g.,

```
  CH2OH         CH2OH         CH2OH
  |             |             |
  HOCH          HCOH          HCOH
  |             |             |
  HCOH          HCOH          HCOH
  |             |             |
  HCOH          HCOH          HOCH
  |             |             |
  HOCH          HOCH          HOCH
  |             |             |
  HCOH          HCOH          HCOH
  |             |             |
  HCOH          HCOH          HCOH
  |             |             |
  CH2OH         CH2OH         CH2OH

D-erythro-L-   D-erythro-L-   erythromannooctitol
 galaoctitol    talooctitol
```

```
  CH2OH         CH2OH         CH2OH
  |             |             |
  HOCH          HOCH          HCOH
  |             |             |
  HCOH          HOCH          HOCH
  |             |             |
  HCOH          HCOH          HOCH
  |             |             |
  HOCH          HOCH          HOCH
  |             |             |
  HOCH          HOCH          HCOH
  |             |             |
  HCOH          HCOH          HCOH
  |             |             |
  CH2OH         CH2OH         HOCH
                              |
                              HCOH
                              |
                              CH2OH

D-threo-L-gala  α,α,α-D-gluco-  α,α,α-D-gluco-
 octitol         nonitol         decitol
```

Examples of other compounds within the definition of polyhydric alcohols, among others, are polyglycerols, e.g., condensation products of glycerol in which molecules of glycerol have been condensed to open-chain or cyclic ethers such as $$CH_2OHCHOHCH_2-O-CH_2CHOHCH_2OH$$

and

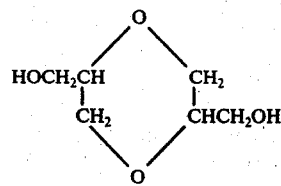

Still further examples of polyhydric alcohols, among others, are pentaerytriol, the inositols or cyclohexanehexols.

Many of the aforementioned polyhydric alcohols occur in various steric configurations and in racemic form as well as in the form of optical isomers. As further defined herein, the term "polyhydric alcohol" includes all such steric and optical isomers as well as mixtures thereof.

As defined herein for the polymerizing agent, the term "halogenated aliphatic alcohols transformable to epoxides in alkaline solution" includes at least one compound illustrated by the following generic formula:

$$CH_2-CH-(CH_2)_n-CH-R^2 \qquad (I)$$
$$\quad |\qquad |\qquad\qquad |$$
$$\quad X\quad\ OH\qquad\quad R^1$$

wherein $n$ is an integer selected from the group consisting of 0,1,2,3, and 4; X is selected from the group consisting of Cl, Br, and I; $R^1$ is selected from the group consisting of OH, Cl, Br, and I; and $R^2$ is selected from the group consisting of H, and if $R^1$ is OH also the radical $-CH_2-X$, wherein X has the meaning specified above. The conversion of these alcohols to epoxides is known in the art [Fairbourne et al., J.P.O.S. pages 1965–1973 (1932)].

The compounds (I) include, among others, compounds of the formula:

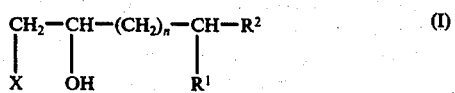

wherein $n$ and X have the meaning specified above, and the compounds (II) in alkaline solution are converted to a diepoxide of the formula:

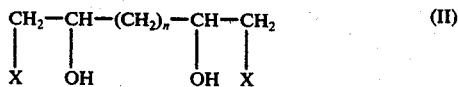

wherein $n$ has the meaning specified above.

Other compounds (I) are dihalohydrins of the formula:

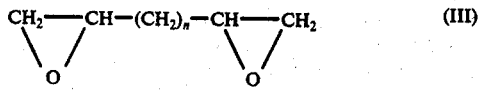

wherein X has the meaning specified above, and the compounds (III) in alkaline solution are converted to compounds of the formula:

wherein X has the meaning specified above.

Still other compounds (I) having the formula:

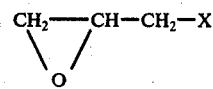

wherein $n$ and X have the meaning specified above, and the compounds (VI) in alkaline solution are converted to compounds of the formula:

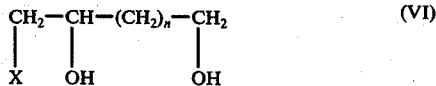

wherein $n$ has the meaning specified above.

Specific compounds (II), among others, are those in which X is Cl and $n$ is 0, X is Cl and $n$ is 1 and X is Cl and $n$ is 2.

Specific compounds (III), among others, are those in which $n$ is 0, $n$ is 1 and $n$ is 2.

Specific compounds (IV), among others, are those in which both X's are chlorine, both X's are bromine and one X is chlorine and the other X is bromine.

Specific compounds (V), among others, are those in which X is chlorine, X is bromine and X is iodine.

Specific compounds (VI), among others, are those in which X is chlorine and $n$ is 0, X is chlorine and $n$ is 1, X is bromine and $n$ is 0 and X is bromine and $n$ is 1.

Specific compounds (VII), among others, are those in which $n$ is 0, $n$ is 1 and $n$ is 2.

The compounds (III), (V) and (VII) are, among others, illustrative examples of epoxides. It is a common feature of polymerizing agents of the compounds (I)-(VII) that they contain at least two reactive groups capable of participating of formation of either linkages. As furgher defined herein, the term "epoxides" inlcude, among other, diepoxides and epoxycarboxylic acids.

The preferred saccharide, as stated heretofore, in sucrose, Preferred polyhydric alcohols are glycerol, polyglycerol, the tetritols, the pentitols, the hexitols and the heptitols. Of the polymerizing agents, the epihalohydrines, particularly epichlorohydrin, are preferred.

The especially preferred combination of reactants is sucrose, sorbitol and epichlorohydrin. Other suitable combinations among others are: trehalose, sorbitol, and epichlorohydrin; raffinose, sorbitol and epichlorohydrin; sucrose, pentaerytritol and epichlorohydrin; glycerol, sucrose and epichlorohydrin; mannitol, sucrose, and epichlorohydrin; dulcitol, sucrose and epichlorohydrin; and hydroxypropylsorbitol, sucrose and epichlorohydrin.

The polymer of the present invention may be prepared by any suitable method. One method is to react in a liquid medium at least one saccharide as defined above, at least one polyhydric alcohol as defined above and at least one polymerizing agent as defined above.

The polymerization is generally carried out in the presence of an alkali, e.g., alkali metal hydroxides. Sodium hydroxide or potassium hydroxide among others, may be used. The alkali may be used either in the form of a solution or in the solid state, for example, in the form of tablets, Alkaline earth metal hydroxides, such as, barium hydroxide, may also be used as the alkali, The preferred alkali is sodium hydroxide.

The polymerization may be carried out in a medium which is inert to the reactant solutions. Examples of such inert media are benzene and white mineral spirits. However, an aqueous solution is the preferred medium.

Any satisfactory proportions of the saccharide, the polyhydric alcohol and the polymerizing agent may be employed. Any satisfactory reaction temperature may also be employed and the reactants may be introduced by any suitable manner. For example, about 0.1 to about 1.0 moles of saccharide and about 0.05 to about 5 moles of polymerizing agent per mole of polyhydric alcohol may be used. In a preferred embodiment of the invention, using sucrose, sorbitol and epichlorohydrin, from about 0.2 to about 1.0 moles of sucrose and from about 0.1 to about 4 moles od epichlorohydrin per mole of sorbitol may be advantageously used.

It may be advantageous to carry out the polymerization by adding the alkali and the polymerizing agent separately to an alkaline aqueous solution of the saccharide and the polyhydric alcohol. However, the alkali and polymerizing agent may also be added continuously to the alkaline solution of saccharide and the polyhydric alcohol in the reaction vessel.

The reaction temperature may be varied over a wide range but in advantageously held between about 20° C. and up to the boiling point of the reaction mixture. The preferred reaction temperature is about 75° C. to 85° C.

The amount of alkali present during the reaction will depend largely upon the amount of added polymerizing agent which is added. In a preferred embodiment of the invention where sorbitol and sucrose are polymerized with epichlorohydrin, the total amount of hydroxyl ions present during the reaction is from about 1.5 to 4.5 moles per mole sorbitol. In the preferred embodiment, sodium hydroxide is used as alkali.

In an especially preferred method for carrying out this reaction, a solution of sucrose and sorbitol in the approximate relative amounts of about 0.1 to 1.0 mole, preferably about 0.5 mole, of sucrose, per mole sorbitol is prepared and made alkaline by addition of sodium hydroxide. To this solution are separately added during the course of the reaction epichlorohydrin and soidum hydroxide in the approximate relative amounts of about 0.1 to 4 moles, preferably about 2 moles, of epichlorohydrin per mole of sorbitol. The temperature of the reaction mixture is raised successively during the reaction up to the desired temperature, e.g., about 75° C to 85° C. After addition of the epichlorohydrin and the sodium hydroxide, the reaction solution is allowed to stand for some time, whereafter the temperature is lowered to about 50° C. and the pH of the reaction mixture is adjusted by addition of a suitable acid, such as HCl, to a value of about 0.6 to 4, usually about 0.65 to 1.0.

The sodium chloride precipitated in the method is removed by filtration and discarded. The remaining reaction mixture is "worked up", i.e., subjected to repeated precipitation and redissolving of the polymer obtained. It is preferred to use ethanol as the precipitating agent, but other organic solvents, such as dioxane, methanol, chloroform, acetone, n-propanol and isopropanol, among others, may be used. The addition of ethanol results in the formation of a twophase system. The aqueous phase contains the desired reaction product. The ethanol phase contains interalia such reaction products having a low molecular weight which are not precipitated. The aqueous phase containing the desired reaction product is thereafter again mixed with water and ethanol, and the resulting aqueous phase collected. This purification and fractionating procedure may be repeated several times, suitably at least five times, whereafter the final product which is the intermediate polymer is diluted with a suitable amount of water in order that a product which is easy to handle may be obtained.

The intermediate polymer, which may or may not be acidified to bring the aldehyde and keto groups into a more reactive state, is reacted with a cyanide to add cyanide ions to the aforementioned carbonyl groups in the intermediate polymer thereby forming a cyanohydrin compound. This can be demonstrated by the following equation:

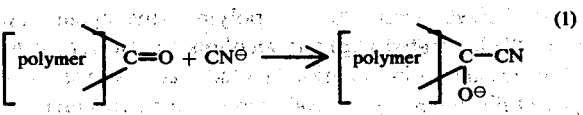

Any suitable source of cyanide ion can be employed as a reactant such as KCN, NaCN, NH$_4$CN. HCN, Ca(CN)$_2$. The amount of cyanide which is used will depend on the amount of carbonyl groups present and should be at least equimolar with the amount of carbonyl groups and preferably in slight excess. For example, about 10% excess of cyanide ions, can be added. Preferably, the reaction is performed in aqueous solution, but it can also be performed in highly polar organic solvents such as pyridine. The reaction with the cyanide ion is suitably carried out at a pH of from 7 to 11, preferably at a pH of about 9. The reaction temperature may vary but a temperature ranging from about 20° C to about 50° C is usually acceptable. The reaction rate increases with the temperature, but at temperatures above about 50° C the cyanide reactant may be hydrolysed.

The cyanide product from equation (1) above is then acidified in accordance with the following equation:

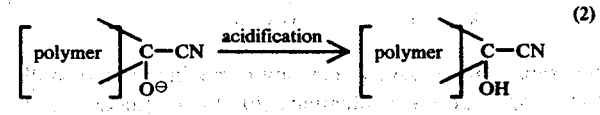

In this acidification step, the pH is lowered to a value below. 7. Any suitable acid, such as HCl and H$_2$SO$_4$, can be used. The acidification can be carried out at a temperature from 0° C up to the boiling point of the reaction mixture. The choice of reaction conditions will vary depending upon the particular cyanide used.

After the acidification is completed, the product is then hydrolyzed as illustrated in the following equation:

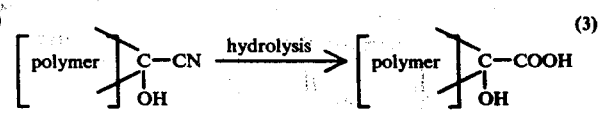

Hydrolysis is known in the art. It can be carried out either by heating the reaction mixture with simultaneous bubbling of air on nitrogen through the solution, or the hydrolysis can be carried out by addition of a suitable acid such as HCl or $H_2SO_4$. Preferably the hydrolysis is performed by heating the reaction solution to a temperature between about 90° C. to 100° C.

In alternative methods, the acidification and hydrolysis in aforementioned equations (2) and (3), respectively, can occur almost simultaneously. The reaction product obtained in equation (1) above can be hydrolysed directly. If desired, however, the hydrolysis may be facilitated by removing, for example by ion exchange, any excess of cyanide ions before the hydrolysis.

The reaction product obtained from hydrolysis can be used directly for the preparation of the iron complex.

In the polymerization reaction according to the present invention a mixture of reaction products with widely varying molecular weights is obtained. It is not possible to ascribe a precise, unitary chemical structure to the reaction product. The molecular weight distribution of the immediate reaction product obtained after the polymerization process is completed may as indicated above, be changed, by removing low molecular weight components. For characterizing the product, therefore, the terms and methods described herebelow have been used. The expression "final product" used herebelow denotes the polymer product obtained after the working up procedure, including the optional addition of water as mentioned above.

A. Loss of Weight on Drying

This is obtained by drying the final product at about 105° C. until constant weight is obtained. The loss of weight is given in percent by weight calculated on the final product.

B. Content of Water in the Final Product This is determined by the Karl Fischer method which is described inter alia in Pharmacopoeia Nordica volume 1 page 75. The content of water is given in percent by weight calculated on the final C. Content of Sodium ($Na^+$) in the Final Product This is determined using a flame spectrophotometer and given in percent by weight calculated on the final product in dried form.

D. Content of Chloride Ions ($Cl^-$) in the Final Product

This is determined by potentiometric titration and is given in percent by weight calculated on the final product or on the final product in dried form. The amounts of $Na^+$ and $Cl^-$ which are given indicate the amount of salts present in the polymer preparation and do not mean that chloride ions are present in the polymer molecule.

E. Content of Organic Dry Substance in the Final Product

This is calculated as the weight of the final product excluding the loss of weight on drying and excluding the weight of $Na^+$ and $Cl^-$ and is given in grams or in percent by weight calculated on the final product.

F. Gel filtration

The molecular weight distribution of the final product is estimated by gel filtration on Sephadex ® G:15, G:25 or G:50. A sample consisting of an amount of final product corresponding to about 100 mg. of organic dry substance is dissolved in 4 ml. of water, added to the column of Sephadex ® used and eluted with water. The eluate is analyzed for content of organic dry substance by measuring the extinction at 700 m$\mu$ of a mixture of 0.5 ml. eluate and 5 ml. of a solution of 0.8 g.$K_2Cr_2O_7$ in 10 ml. $H_2O$ and 200 ml. conc. $H_2SO_4$. The extinction measured is corrected against a blank and plotted against the volume of eluate. The diagram obtained is a measure of the molecular weight distribution. The eluate is also tested for contents of $Cl^-$. This gel filtration test is well known in the art as evidenced by "Sephadex, Theory and Experimental Technique" published by Pharmacia Fine Chemicals, Uppsala, Sweden.

G. Content of Carboxylic Groups in the Final Solution

This is determined by passing aqueous solution of polymer through strongly acidic cation exchanger and titrating for total contents of acid with NaOH.

H. Iron-Complex-Forming Capacity of the Final Product

This may be determined by using the following solutions:

| | | |
|---|---|---|
| (I) | Distilled water | 225 ml. |
| | Lactic acid | 90 ml. (1.20 mole) |
| | Sodium hydroxide | 148 ml. (0.90 mole) |
| | Polymer (organic dry substance) | 202.5 g. |
| (II) | Sodium hydroxide | 288 g. (7.3 mole) |
| | Distilled water | 1200 ml. |
| (III) | Ferric chloride hexahydrate $FeCl_3 . 6H_2O$ | 270 g. (1.0 mole) |
| | Distilled water | 450 ml. |
| (IV) | Hydrochloric acid 6N | about 150 ml. |
| (V) | Distilled water | about 2.21 |
| (VI) | Ethanol 95.5% (volume percent) | about 14.8 ml. |

Separate solutions of the ferric chloride, the sodium hydroxide and the polymer were prepared. The lactic acid (90 ml.), 2/3 of the volume of water (150 ml.) and the sodium hydroxide (148 ml.) were mixed separately before the polymer was added. The rest of the water (75 ml.) was used for rinsing the vessels whereafter it was added to the solution. The mixture (I) thus obtained was heated to 80° C with stirring.

To the mixture (I) were added alternately with vigorous stirring 9 × 90 ml. portions of the sodium hydroxide solution (II), in total 4.86 mole NaOH, and 9 × 60 ml. portions of the ferric chloride solution (III), in total 1.0 mole. The addition was carried out dropwise during 1 minute for the sodium hydroxide and dropwise during 2 minutes for the ferric chloride solution. Between each addition a delay of 2 minutes was made. One minute after the final addition of ferric chloride solution, 167 ml. (0.98 mole) of sodium hydroxide (II) was added. The temperature of the reaction mixture was thereafter kept at 80° C. for 35 minutes, whereafter the mixture was cooled to 25° C. Thereafter, the volume of the reaction mixture was adjusted to 2250 ml. using distilled water, whereupon 5100 ml. ethanol was added during 15–30 minutes with vigorous stirring. Thereafter, the stirring was continued for 10 minutes more. The precipitate obtained was allowed to settle for 30–60 minutes, after which the mother liquor was sucked off. The precipitate was filtered off and washed once with 900 ml. diluted ethanol (2 volumes of ethanol + 1 volume of distilled water). Thereafter, the precipitate was dissolved by adding it while stirring to 1350 ml. of distilled water heated to 40° C. After addition of the precipitate, the solution was heated to 80° C. in about 30 minutes. Thereafter, the mixture was kept at 80° C. while stirring for 30 minutes more.

The solution was thereafter cooled to 25° C. and neutralized using 6N hydrochloric acid IV added dropwise with vigorous stirring during 20–25 minutes until the pH of the mixture was 6.2. Usually, 140–150 ml. of hydrochloric acid was necessary. The reaction mixture was freed from undissolved matter, whereafter, the volume was adjusted with distilled water (V) to 2100 ml. A second precipitation was carried out by adding to the solution with stirring 4575 ml. of ethanol (VI) during 15–20 minutes. Stirring was continued for 2 minutes more. The precipitate was allowed to settle overnight. Thereafter, the mother liquor was sucked off and the solid was sucked off and washed three times using 900 ml. of diluted ethanol (ethanol: water 2:1) and three times with undiluted ethanol (900ml.), whereafter it was dried in vacuum at 40° C. for 4–5 hours or overnight.

The following parameters were determined in the dried iron preparation:

1. Yield of dried iron preparation, measured in grams.
2. Yield of complex-bound iron, calculated in percent of the total amount of ferric iron added during the reaction.
3. Contents of iron in the dried iron preparation, percent by weight calculated on the dried iron preparation.

I. Resorption in Rabbit of Intramuscularly Administered Injection Solution

The injection solution of the dried iron preparation obtained as described in paragraph H above was prepared according to the following method. Distilled water (125 ml.) was heated to 80° C. in a 3-necked round-bottomed flask provided with cooler, thermometer and stirrer. Dried iron preparation obtained as described above was added in small portions during 15 minutes with vigorous stirring. Dried preparation corresponding to 7.5 g. of iron was added. The solution thus obtained was kept at 80° C. for 50 minutes, whereafter it was cooled to 25° C. After dilution with distilled water to 150 ml. the solution obtained was filtered, filled into 10 ml. ampoules and sterilized at 120° C. for 20 minutes. The injection solution obtained had a total content of iron of about 50 mg/ml.

The resorption tests on rabbits were carried out in the following way. The injection solution was injected in doses of 20 mg. Fe per kg. body weight deep into the glutei of rabbits. Male albino rabbits weight 2 to 3 kg. were consistently used. The animals were killed at different time intervals after injection and the gluteal muscles were dissected away from the leg. Musculature and skin around the injection site were wet oxidized with sulphuric acid and nitric acid, and the iron content was then determined by means of a colorimetric rhodanide method. It was found that the iron was resorbed very rapidly. In most cases, more than 60% of the administered iron had been resorbed after 24 hours; more than 85% of the iron had been resorbed after 7 days; and more than 90% of the iron had been resorbed after 14 days. It was also found that the amount of iron which was excreted after 24 hours usually was less than 15%. Thus, it is shown that iron preparations for intramuscular injection prepared using the polymer of the present invention as stabilizing agent compare favorably with presently existing and marketed intramuscularly administrable iron preparations. It can be concluded from the results of gel filtration on Sephades ® G:15, G:25 and G:50 gels that the average moleculr weight of the polymer in the form called "final product" is in the range 700 to about 5000. It has also been established that polymers, which according to gel filtration tests have an average molecular weight in the range from about 1500 to about 5000, provide iron complexes, which in the form of injection solutions, give a particularly advantageous response with regard to resorption and excretion when tested on rabbits.

J. Intrinsic Viscosity of the Polymer

This in many cases was found to be in the range from about 0.020 to about 0.080 dl/g. It is determined according to well know procedures [Flory, Principles of Polymer Chemistry (1953)].

Thus, in accordance with the present invention a new polymer has been prepared which a. is soluble or swellable in water;
b. is physiologically innocuous;
c. has capability of reacting with polyvalent metals cations such as $Fe^{3+}$, $Al^{3+}$, $Sb^{3+}$, $Bi^{3+}$, $Zr^{4+}$, $Sn^{4+}$, $Ti^{4+}$, $Bi^{2+}$, and $Ca^{2+}$, or mixtures thereof, with formation of a complex between the polymer and the metal cation; and
d. has the capability of stabilizing ferric iron in aqueous solutions intended for intramuscular or intravenous injection of mammals including man.

The preferred embodiment of the invention, is the polymer built up by sucrose, sorbitol and epichlorohydrin, and furthermore e. contains from about 0.2 to about 1.5 milliequivalents of carboxyl groups per gram organic dry substance,
f. has an average molecular weight, as estimated by gel filtration, in the range from about 700 to about 5000.

The polymer of the present invention is particularly valuable and useful as a stabilizing agent for iron preparations intended for intramuscular injection. The use of the polymer as such a stabilizing agent is an important aspect of the present invention. The polymer may be also used, among other uses, as a. a viscosity — regulating agent in foodstuffs, pharmaceuticals, herbicides and similar preparations, or in washing agents;
b. a substitute for blood plasma;
c. a carrier substance for biologically active substance such as enzymes;
d. a polymer— metal ion complex as a soil improving material;
e. a liquid cement or glue;
f. a starting material in the preparation of plastic materials;
g. a precipitation — or flocculation — inhibiting agent in the production of beer;
h. an additive to electrolytes;
i. a detoxifying agent.
j. in combination with suitable substances, such as $Ba^{2+}$, used as an X-ray contrast agent.

Another embodiment of this invention is iron preparations for intramuscular injection wherein the aforementioned polymer is used as stabilizing agent. A dry iron-containing composition which can be "worked up" into a preparation suitable for intramuscular injection in human and veterinary medicine is prepared by reacting in alkaline aqueous solution;

a. at least one water-soluble, ferric salt and
b. a physiologically innocuous, water swellable polymer prepared as described previously and capable of forming complexes with ferric iron at an alkaline pH, whereafter the iron-containing complex is precipitated and the precipitate is purified and dried. The reaction between the ferric salt and the polymer is carried out at a pH to provide, by addition of alkali, at the end of the reaction a pH of about 10 to 14.

The invention also includes liquid iron-containing compositions comprising an aqueous solution of the dry iron-containing composition obtained as described above. The compositions are readily soluble at physiological pH values and are sufficiently stable for the solutions to be sterilized by autoclaving.

The iron must be in the trivalent form since ferrous compounds do not give the desired stability. Suitable ferric compounds, among others, include ferric chloride, ferric nitrate, ferric sulphate and ferric acetate, and double salts (e.g., ferric ammonium sulphate and ferric potassium sulphate) and mixtures thereof.

The dried compositions may contain from about 5% to 40%, especially about 20% to 36%, by weight of iron and the injectable solutions may contain from about 5 to about 100 milligrams of iron per milliliter, especially about 50 milligrams of iron per milliliter. It is generally desirable that the iron concentration in the injection solution should be as high as possible, in order that the injected volume may be small. In some cases, however, less concentrated preparations may be more suitable.

The polymer used as stabilizing agent in the iron preparations is preferably built up by reacting, in the manner described herein, at least one saccharide selected from the group consisting of sucrose, trehalose and raffinose, at least one polyhydric alcohol selected from the group consisting of glycerol, polyglycerols, tetritols, pentitols, hexitols, heptitols, and hydroxylow-eralkyl, hexitols and heptitols derived therefrom, at least one polymerizing agent selected from the group consisting of epichlorohydrins and diepoxides. The preferred polymer is built up by sucrose, sorbitol, and epichlorohydrin as previously described.

The dry iron preparation is prepared by reacting in aqueous solution a polymer prepared as described previously, with the aforementioned water-soluble ferric compound, preferably ferric chloride, whereafter the iron-containing complex thereby obtained is precipitated and the precipitate is purified and, if desired dried. The pH of the reaction mixture is adjusted to provide a value of about 10 to 14 at the end of the reaction. The amount of polymer used in the reaction may be in the range from about 1 to about 15 g., preferably from about 3 to about 6 g., calculated as dried product per gram of iron, depending on the particular polymer used. The reaction temperataure suitably is in the range from about 0° C. to about 100° C. depending on the particular embodiment used. In the first embodiment described herebelow, the temperature is preferably at about 80° C. The pH of the acidic reaction mixture is successively increased during the reaction to a value of about 10 to 14. As the alkali, sodium hydroxide may advantageously be used. The precipitation of the iron complex from the reaction solution is effected using a nonsolvent for the complex. Ethanol is used suitably. If the solution of the iron complex is to be used directly, the complex is not precipitated after the final dissolution.

Besides water-soluble ferric compounds, ferric compounds which are slightly or very slightly soluble in water may be used, for example, freshly prepared ferric hydroxide, ferric carbonate and ferric lactate.

For purification of the precipitate, redissolution is conveniently carried out by adding the precipitate to distilled water at a temperature of about 40° c. The temperature is subsequently raised to about 80° C., and kept there for some time. Thereafter, the solution is cooled to room temperature and the pH is adjusted from about 5.5 to about 10, preferably to about 6 to about 8, with a suitable acid, such as HCl.

In one embodiment of the process for preparing the dry iron preparation, an alkaline aqueous solution of the polymer, and optionally lactic acid, is prepared. Lactic acid may be added in an amount from 0 to about 10 g. per gram of iron. The mixture is thereafter heated to about 800° C. and portions of the ferric compound in aqueous solution and portions of alkali in aqueous solution are interchangeably added. In this way, the pH of the reaction mixture is consistently kept alkaline. The polymer is added in an amount corresponding to from about 1 to about 15 calculated as dried substance, per gram of iron. Preferably, from about 3 to about 6 g. of polymer, calculated as dried product, are used per gram of iron. The reaction mixture may thereafter be allowed to stand for some time and thereafter cooled to room temperature. The iron complex formed is thereafter precipitated using a non-solvent for the complex, suitably ethanol. The precipitate formed is separated. It is purified by repeated dissolution in water, precipitation and washing. It is finally dried.

In another embodiment of the process for preparing the dry iron preparation, a first aqueous solution containing the polymer and the total amount of the ferric salt to be used is prepared. From about 1 to about 15 g. of polymer per gram iron is used in said first aqueous solution. The preferred ratio is from about 3 to about 6 g. polymer per g. iron. To the acidic solution thus obtained, to which lactic acid suitably is not added, alkali is successively added at a suitable temperature in the range of from about 0° C. to 60° C. When all alkali has been added, the temperature of the reaction mixture is raised to about 80° C., kept there for some time, and subsequently lowered to about 25° C. The iron complex formed is thereafter worked up by precipitation and redissolution as described previously, with the exception that some further polymer in alkaline aqueous solution is suitably added at each redissolution. For example, if two precipitations and redissolutions are carried out, about one fourth of the amount of initially added polymer may be added during each redissolution.

When preparing an injection solution of the dry iron preparation, the dry iron preparation is dissolved in water and sterilized by autoclaving. The dry iron preparation is added in portions, with stirring, to distilled water at a temperature of about 80° C. When all the dry iron composition has been added, the temperature is kept at 80° C. for some additional time, for example, about 50 minutes, whereafter the solution is cooled to about 25° C., optionally diluted with distilled water, filtered, and filled in bottles which are autoclaved at about 120° C. for about 20 minutes. A typical preparation thus obtained contains about 5 to 100, e.g., 50, mg. iron per ml.

As is evident from the following examples, the iron preparations in the form of sterilized injection solutions are well resorbed when tested on rabbits, while at the same time the excretion of iron is low, often less than 15% 24 hours after the administration. The acute i.p. toxicity in mice of the injectable iron preparations has been found to be in the range 300 to 500 mg. per kg. of bodyweight. The acute i.p. toxicity in mice of Jectofer ® as tested on the same strain of mice is about 50 mg per kg. of bodyweight. The low toxicity of the iron preparation according to the present invention in combination with its high resorption and low excretion makes it possible to administer it to human patients in unit dosages containing more than 500 mg. iron. Two such dosages may be given to each patient at a single occasion.

The correlation of test results in this field between the treatment of animals, e.g., rabbits, and the treatment of human beings is substantiated in the art as evidenced by Lindvall, Andersson, "Studies on a New Intramuscular Haemativic Iron-Sorbitol", British Journal of pharmacology and Chemotherapy, 17, 358–371 (1961) and Andersson "Clinical Investigations on a New Intramuscular Haematic", British Medical Journal, 275–279 (July 29, 1961).

The invention is illustrated further by the following examples.

EXAMPLE 1

To a round-bottomed flask, volume 5 liter, provided with stirrer, dropping funnel, thermometer and cooler were added at 45° C.

150 ml. distilled water
34 g. NaOH
300 g. sorbitol
150 g. sucrose

Then 200 ml. epichlorhydrin was added continuously during 55 min. The temperature was raised to 75° C. during 20 min. as calculated from the start of addition of the epichlorhydrin. The temperature of 75° C. is retained during the polymerization, which is carried out with effective stirring.

As shown in Table 1, materials were added in the following portions: 85 g. NaOH in solid form; 20 g. NaOH dissolved in distilled water to a volume of 28 ml. and 55 ml. epichlorhydrin.

Furthermore, 250 ml. benzene and 200 ml. distilled water were added because of the increasing viscosity of the reaction mixture during the court of the reaction.

TABLE 1

| Time (min) | Amount of epichlor- hydrin added (ml.) | Amount of NaOH added (g.) | Amount of NaOH- solution added (g.) | Amount of benzene added (ml.) | Amount of distilled water added (ml.) |
|---|---|---|---|---|---|
| 60 | | 5 | | | |
| 75 | | 10 | | | |
| 90 | | 10 | | | |
| 105 | | 10 | | | |
| 120 | | 10 | | | |
| 135 | | 10 | | | |
| 150 | 50 | | | | |
| 165 | | 10 | | | |
| 180 | | 10 | | | |
| 195 | | 10 | | | |
| 210 | | | 14 | | |
| 225 | | | 14 | | |
| 240 | 5 | | | | |
| 246 | | | | 250 | |
| 248 | | | | | |

At 285 min. the cooling of the reacton mixture was started simultaneously with slow addition of 50 ml. 4M HCl. 100 ml. 6M HCl is thereafter added whereby the polymer forms an easily removable suspension in the benzene-water mixture. At 305 min. the temperature is 56° C. in the reaction mixture and at 330 min. the cooling is stopped. The temperature is then 30° C. Then 70 ml. 2 M NaOH is added and the pH is 0.0 measured after 15 min. The reaction mixture is filtered through double filter papers. The filtration which was very slow was allowed to continue over night.

The next day the filtration was finished and the filtrate had formed two phases. On the filter a small amount of an adhesive rest remains. The different fractions are defined as follows:

Filtrate, benzene phase designated as F 1, discarded.
Filtrate, water phase designated as F 2.
Remainder on filter designated as F 3, discarded.

The F 2 fraction was strongly opalescent and was theretofore filtered through Zeiss filter plate Ko 2. The filtrate was still opalescent but to a considerably diminished degree compared with the opalescence before the filtering. The fractions were:

Filtrate designated as F 4, volume 1070 ml.
Remainder designated as F5, minute amount, discarded.

The F 4 fraction was diluted with water to 1200 ml. and the pH ws 0.02. Then 3000 ml. ethanol, 99.5% was added with vigorous stirring whereupon the mixture was allowed to stand for 60 min. to form:

Mother liquor designated as F 6, discarded.
Remainder designated as F 7, volume 750 ml.

The F 7 fraction was mixed with 150 ml. distilled water and 1500 ml. ethanol, 99.5%. The mixture was allowed to stand for 2 hours to provide:

Mother liquor designated as F 8.
Remainder designated as F 9, volume 650 ml.

The F 9 fraction was mixed with 325 ml. distilled water. The mixture was stirred for 10 min. and thereafter 1300 ml. ethanol, 99.5%, was added. The mixture was allowed to stand for 30 min. and the fractions were as follows:

Mother liquor designated as F 10.
Remainder designated as F 11, volume 630 ml.

The F 11 fraction was mixed with 315 ml. distilled water and with 1260 ml. ethanol, 99.5%, whereafter the mixture was allowed to stand for 40 min. to form:

Mother liquor designated as F 12.
Remainder designated as F 13, volume 500 ml.

The F 13 fraction was mixed with 100 ml. distilled water and 1000 ml. ethanol, 99.5%. The mixture was allowed to stand for 30 min. to provide:

Mother Liquor designated as F 14.
Remainer designated as F 15.

The F 15 fraction was washed three times with 150 ml. ethanol, 99.5%, whereupon it was dried in vacuum at 50° C. for 60 min. in order to remove rest of the ethanol. The dried F 15 fraction was diluted with distilled water to 493 g. to form a product which was analyzed as follows:

| | |
|---|---|
| Loss of weight at drying 32.7% | |
| Contents of $Na^+$ | 4.7% calculated on dried sample. |
| Contents of $Cl^-$ | 4.2% calculated on dried sample |

EXAMPLE 2

Solution I was formed from 273 g. of the product prepared in Example 1, which contained reducing groups corresponding to 18 g. glucose, 500 ml. distilled water and 0.5 ml. 25% $NH_4OH$. Solution II was provided from 15 g. KCN corresponding to the double equivalent amount of glucose plus about 10% glucose in excess, calculated on 18 g. glucose in 50 ml. distilled water.

Solution I was added to round-bottom flask provided with magnet stirrer, dropping funnel, thermometer, and cooler with receiver. Solution II was added to solution I at room temperature and was allowed to stand for 30 minutes. Thereafter the temperature was raised to 40° C. and was kept there during 120 min. The solution was then allowed to cool and was allowed to stand at room temperature for 3 days. The temperature was subsequently to 70° C. in 90 min., while a stream of air simultaneously was passed through the solution. After 15 min. at 70° C. the heating was interrupted and the temperature was allowed to drop to 30° C. 2 M HCl was added slowly with vigorous stirring to form a pH of about 6.

Thereafter, the solution was heated again to about 70° C. during simultaneous aeration. After repeated heating and aeration, which was carried out during 60 min. the solution was allowed to cool to room temperature whereafter pH was adjusted to about 1 with 2 M HCl. The acidified solution was allowed to stand to the next day and its was then heated to 70° C. during 30 min. After cooling, the solution was tested for presence of cyanide ions.

The test indicated that no cyanide ions were present. The solution was evaporated in vacuo to about half its volume whereupon the pH was adjusted to 5 using $NaHCO_3$. Ten grams of active carbon was added during stirring. After 15 min. the mixture was filtered through Zeiss filter plate No. Ko2. The filterplate was washed with distilled water. The washing water was mixed with the filtrate and the resulting mixture was evaporated in vacuo to about 250 ml. Two volumes of ethanol, 99.5%, were added whereupon the mixture was allowed to stand for 30 min. Thereafter two phases had formed as follows.

Light phase designated as F 1.
Heavy phase designated as F 2, volume 230 ml.
The F 2 phase was mixed with 1/5 volume distilled water and with 2 volumes of ethanol, 99.5%. The mixture was allowed to stand for 30 min., whereby 2 phases were formed as follows:

Light phase designated as F 3.
Heavy phase designated as F 4.
The F 4 phase was mixed with ½ volume distilled water and with 2 volumes of ethanol, 99.5%. The mixture was allowed to stand for 30 min. whereby the following 2 phases separated:

Light phase designated as F 5.
Heavy phae designated as F 6, volume 210 ml.
The F 6 phase was mixed with 21 ml. distilled water and with 105 ml. ethanol, 99.5%. After 30 min. the resulting light phase (F 7) was decanted. The resulting heavy phase (F 8) was washed twice with 105 ml. ethanol, 99.5%, and three times with acetone, whereupon it was dried in vacuo in order to remove remaining rests of acetone. The dried fraction was diluted with distilled water to 231 g.

The product was analyzed as follows:

| | |
|---|---|
| Loss of weight at drying | 35.5% |
| Contents of $K^+$ | 3.3% calculated on dried sample. |
| Contents of $Na^+$ | 2.6% calculated on dried sample. |
| Contents of $Cl^-$ | 6.2% calculated on dried sample. |
| Contents of Carboxyl groups | 0.54 milliequivalents g. organic dry substance. |

EXAMPLE 3

This example is concerned with the preparation of a dry iron preparation.

The polymer of Example 2 corresponding to 60 g. of organic dry substance was dissolved in 300 ml. of distilled water at room temperature. A solution containing 60 g. $FeCO_3.6H_2O$ in 100 ml. of distilled water was mixed with the polymer solution at room temperature.

To the mixture obtained was added under stirring 1000 ml. 1M NaOH. After 70 minutes at room temperature, the temperature of the mixture was raised to 80° C. The mixture was kept at this temperature for 20 minutes whereupon it wall cooled to room temperature and filtered through Seitz filter plate Ko2. The filtrate was diluted with distilled water to 1900 ml. whereafter 3800 ml. 99.5% ethanol was added under vigorous stirring. After 20 minutes, the precipitate obtained was filtered off and dissolved in a mixture of 600 ml. distilled water, 15 g. polymer calculated as organic dry substance, and 20 ml. 1M NaOH. The temperature was raised to 80° C. and kept there for 25 minutes, whereafter the solution was cooled to room temperature. To the cooled solution 1M HCl was added with vigorous stirring until a pH of 6.7 was obtained. The solution was filtered through Seitz filter plate EKS. The filter plate was washed with distilled water, which was mixed with the filtrate. The pH of the mixture was adjusted from 7.7 to 7.3 using 1M HCl. The volume was then adjusted with distilled water to 1000 ml. and 2000 ml. ethanol, 99.5%, was added with vigorous stirring. After 30 minutes the precipitate obtained was filtered off and washed with 100 ml. ethanol diluted to the same concentration as the mother liquor and with 100 ml. ethanol diluted to 75% and finally three times with 150 ml. ethanol, 99/5%. The washed precipitate was dried in vacuum at 50° C.

The yield was 74 g. The total content of Fe was 22.8% calculated on the original sample.

EXAMPLE 4

In this example an injection solution was prepared.

To a round-bottomed flask, volume 500 ml., provided with stirrer, thermometer and cooler, 130 ml. distilled water was added and heated to 80° C. Then 32.9 g. of the dry iron preparation of Example 3 was added to the water for 10 min. with stirring. The temperature of the mixture was kept at 80° C. for 70 min. calculated from the start of addition of the dry iron preparation. The solution obtained was cooled thereafter to room temperature and the pH was adjusted to 7.6 using 1M HCl. The volume was adjusted subsequently to 150 ml. with distilled water. The solution was thereafter filtered through Zeiss filter plate Ko2 and through Pyrex glass filter. The filtrate was filled on ampoules and autoclavated at 120° C. for 20 min.

| Analysis: | | |
|---|---|---|
| Total amount of Fe | 50.5 | mg/ml |
| Amount of $Fe^{2+}$ | 0.98 | mg/ml |
| Viscosity | 10.7 | cPs |
| pH | 7.7 | |

The resorption of Fe from rabbit muscle after 7 days was 86%. The excretion of Fe in the urine of the rabbit during the first 24 hours after the injection was 2%.

Having set forth the general nature and specific embodiments of the present invention, the scope is now particularly pointed out in the appended claims.

What is claimed is:

1. A process for preparing a polymer which is suitable for being administered parenterally which comprises:
   A. reacting in an aqueous solution at a temperature between about 20° C and the boiling point of the reaction mixture 1. about 0.1 to 1.0 moles of a saccharide (per mole of component (3) below) which is selected from the group consisting of
   a. sucrose,
   b. trehalose, and
   c. raffinose;
2. about 0.05 to 5 moles of a polymerization agent (per mole of component (3) below) of the formula

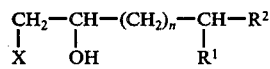

wherein n is an integer selected from the group consisting of 0, 1, 2, 3 and 4; X is selected from the group consisting of Cl, Br and I; R$^1$ is selected from the group consisting of OH, Cl, Br and I; and R$^2$ is selected from the group consisting of H and CH$_2$X with the proviso that R$^2$ is CH$_2$X only when R$^1$ is OH, wherein X has the meaning specified above; the epoxides or the diepoxides derivable therefrom; and
3. a hexitol selected from the group consisting of sorbitol, hydroxypropyl sorbitol, mannitol, talitol, iditol, galactitol, and allitol to form a first intermediate of the formula (polymer) >C=O    (I);

B. reacting said first intermediate product with a cyanide selected from the group consisting of KCN, NaCN, Ca(CN)$_2$, HCN, and NH$_4$CN in an amount at least equimolar with the amount of carbonyl groups on the first intermediate product to form a second intermediate product of the formula

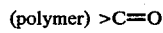

C. acidifying said second intermediate product to form a third intermediate product of the formula

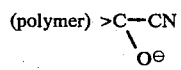

D. hydrolyzing said third intermediate product to form a water swellable polymer of the formula

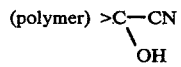

2. A polymer suitable for being administered parenterally which has been prepared by
A. reacting in an aqueous solution at a temperature between about 20° C and the boiling point of the reaction mixture
   1. about 0.1 to 1.0 moles of a saccharide (per mole of component (3) below) which is selected from the group consisting of
      a. sucrose,
      b. trehalose, and
      c. raffinose;
   2. about 0.05 to 5 moles of a polymerization agent (per mole of component (3) below) of the formula

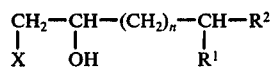

wherein n is an integer selected from the group consisting of 0, 1, 2, 3 and 4; X is selected from the group consisting of Cl, Br and I; R$^1$ is selected from the group consisting of OH, Cl, Br and I; and R$^2$ is selected from the group consisting of H and CH$_2$X with the proviso that R$^2$ is CH$_2$X only when R$^1$ is OH, wherein X has the meaning specified above; the epoxides or the diepoxides derivable therefrom; and
   3. a hexitol selected from the group consisting of sorbitol, hydroxypropyl sorbitol, mannitol, talitol, iditol, galactitol, and allitol to from a first intermediate of the formula (polymer) >C=O    (I);

B. reacting said first intermediate product with a cyanide selected from the group consisting of KCN, NaCN, Ca(CN)$_2$, HCN, and NH$_4$CN in an amount at least equimolar with the amount of carbonyl groups on the first intermediate product to form a second intermediate product of the formula

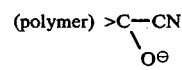

C. acidifying said second intermediate product to from a third intermediate product of the formula

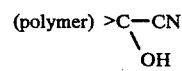

D. hydrolyzing said thrid intermediate product to form a water swellable polymer of the formula

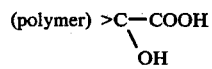

3. The polymer according to claim 2 wherein the polymerization agent is selected from the group consisting of (a) $\begin{array}{c} CH_2-CH-(CH_2)_n-CH-CH \\ | \quad\; | \quad\quad\quad\quad | \quad\; | \\ X \quad OH \quad\quad\quad OH \; X \end{array}$ (V);

(b) $\begin{array}{c} CH_2\!-\!\!-\!\!-\!CH-(CH_2)_n-CH\!-\!\!-\!\!-\!CH_2 \\ \diagdown \;\, \diagup \quad\quad\quad\quad \diagdown \;\, \diagup \\ O \quad\quad\quad\quad\quad\;\; O \end{array}$ (VI);

(c) $\begin{array}{c} CH_2-CH-CH_2 \\ | \quad\; | \quad\; | \\ X \quad OH \; X \end{array}$ (VII);

(d) $\begin{array}{c} CH_2\!-\!\!-\!\!-\!CH-CH_2-X \\ \diagdown \;\, \diagup \\ O \end{array}$ (VII$_1$);

(e) $\begin{array}{c} CH_2-CH-(CH_2)_n-CH_2 \\ | \quad\; | \quad\quad\quad\quad | \\ X \quad OH \quad\quad\quad\; OH \end{array}$ (IX);

and

-continued (f) $$CH_2\underset{O}{\underbrace{\phantom{XXX}}}CH-(CH_2)_n-\underset{OH}{CH_2} \quad (XI);$$

wherein n is an integer selected from the group consisting of 0, 1, 2, 3 and 4, and X is selected from the group consisting of Cl, Br and I.

4. The polymer according to claim 3 wherein the polymerization agent is a structure (VIII) compound wherein X is Cl.

5. The polymer according to claim 2 wherein the hexitol is sorbitol.

6. A process for preparing a composition for treatment of iron deficiency by parenteral administration which comprises A. reacting in an aqueous solution at a temperature between about 20° C and the boiling point of the reaction mixture
1. about 0.1 to 1.0 moles of a saccharide (per mole of component (3) below) which is selected from the group consisting of
    a. sucrose,
    b. trehalose, and
    c. raffinose;
2. about 0.05 to 5 moles of a polymerization agent (per mole of component (3) below) of the formula $$\underset{X}{CH_2}-\underset{OH}{CH}-(CH_2)_n-\underset{R^1}{CH}-R^2$$

wherein n is an integer selected from the group consisting of 0, 1, 2, 3 and 4; X is selected from the group consisting of Cl, Br and I; $R^1$ is selected from the group consisting of OH, Cl, Br and I; and $R^2$ is selected from the group consisting of H and $CH_2X$ with the proviso that $R^2$ is $CH_2X$ only when $R^1$ is OH, wherein X has the meaning specified above; the epoxides or the diepoxides derivable therefrom; and 3. a hexitol selected from the group consisting of sorbitol, hydroxypropyl sorbitol, mannitol, talitol, iditol, galactitol, and allitol to form a first intermediate of the formula (polymer) >C=O     (I);

B. reacting said first intermediate product with a cyanide selected from the group consisting of KCN, NaCN, Ca(CN)$_2$, HCN, and NH$_4$CN in an amount at least equimolar with the amount of carbonyl groups on the first intermediate product to form a second intermediate product of the formula $$(polymer) >C-CN \atop O^\ominus \quad (II);$$

C. acidifying said second intermediate product to form a third intermediate product of the formula $$(polymer) >C-CN \atop OH \quad (III);$$

C. hydrolyzing said third intermediate product to form a water swellable polymer of the formula $$(polymer) >C-COOH \atop OH \quad (IV); and$$

E. reacting said water swellable polymer with a ferric compound in solution under alkaline conditions to form a polymer complex of ferric iron.

7. The process according to claim 1 in which the hexitol is sorbitol.

8. The process according to claim 1 in which the polymerization agent is selected from the group consisting of:

(a) $$CH_2-\underset{X}{CH}-(CH_2)_n-\underset{OH}{CH}-\underset{X,mr,4\ CH_2}{CH-} \quad (V);$$

(b) $$CH_2\underset{O}{\underbrace{\phantom{XX}}}CH-(CH_2)_n-CH\underset{O}{\underbrace{\phantom{XX}}}CH_2 \quad (VI);$$

(c) $$\underset{X}{CH_2}-\underset{OH}{CH}-\underset{X}{CH_2} \quad (VII);$$

(d) $$CH_2\underset{O}{\underbrace{\phantom{XX}}}CH-CH_2-X \quad (VIII);$$

(e) $$CH_2\underset{O}{\underbrace{\phantom{XX}}}CH-(CH_2)_n-\underset{OH}{CH_2} \quad (IX);$$

and (f) $$CH_2\underset{O}{\underbrace{\phantom{XX}}}CH-(CH_2)_n-\underset{OH}{CH_2} \quad (XI);$$

wherein n is an integer selected from the group consisting of:
1. 0,
2. 1,
3. 2,
4. 3, and
5. 4; and X is selected from the group consisting of:
1. Cl,
2. Br and
3. I.

9. The process according to claim 8 in which the polymerization agent is a structure (VIII) compound wherein X is Cl.

10. The process according to claim 6 in which the first intermediate product is acidified prior to the reaction with a cyanide.

11. The process according to claim 6 in which the acidifying step and hydrolyzing step occur substantially simultaneously.

12. The process according to claim 6 in which the reaction with the ferric compound is performed at a temperature of about 0° to 100° C.

13. A process according to claim 6 wherein the reaction between the ferric compound and the polymer is carried out at a pH of about 10-14.

14. A process according to claim 6 wherein the ferric iron complex formed is precipitated at least once with ethanol whereafter the precipitated iron complex is separated from the mixture.

15. A process according to claim 6 wherein a solution of lactic acid is added to the swellable polymer before the reaction of the polymer with the ferric compound.

16. A process according to claim 15 wherein the ferric compound and alkali are in aqueous solutions and said solutions of ferric compound and alkali are added separately to an aqueous solution of the polymer and lactic acid.

17. A process according to claim 6 wherein the alkali in aqueous solution is added to an aqueous solution containing the polymer and the ferric compound.

18. A process according to claim 6 wherein further polymer in alkaline solution is added at each dissolution of the ferric iron complex.

19. The process according to claim 6 wherein trehalose is the saccharide, sorbitol is the hexitol, and epichlorohydrin is the polymerization agent.

20. The process according to claim 6 wherein raffinose is the saccharide, sorbitol is the hexitol, and epichlorohydrin is the polymerization agent.

21. The process according to claim 6 wherein sucrose is the saccharide, mannitol is the hexitol, and epichlorohydrin is the polymerization agent.

22. The process according to claim 6 wherein sucrose is the saccharide, galactitol is the hexitol, and epichlorohydrin is the polymerization agent.

23. The process according to claim 6 wherein sucrose is the saccharide, hydroxypropylsorbitol is the hexitol, and epichlorohydrin is the polymerization agent.

24. The process process according to claim 6 wherein sucrose is the saccharide, sorbitol is the hexitol, and epichlorohydrin is the polymerization agent.

25. The process according to claim 6 wherein the polymerization agent is selected from the group consisting of

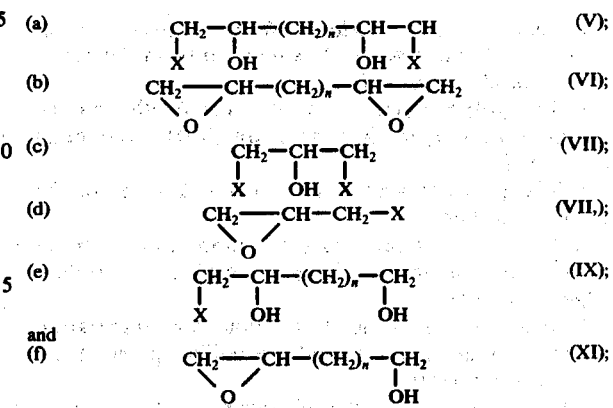

wherein $n$ is an integer selected from the group consisting of 0, 1, 2, 3 and 4, and X is selected from the group consisting of Cl, Br and I.

26. The process according to claim 25, wherein the polymerization agent is a structure (VIII) compound wherein X is Cl.

* * * * *

UNITED STATES PATENT AND TRADEMARK OFFICE
CERTIFICATE OF CORRECTION

PATENT NO. : 4,056,672
DATED : November 1, 1977
INVENTOR(S) : Alf-Goran Dahlberg et al.

It is certified that error appears in the above-identified patent and that said Letters Patent are hereby corrected as shown below:

Column 20, line 21, in claim 2, "from" should read -- form --;

line 45, in claim 2, "thrid" should read -- third --;

line 64, in claim 3, "(VII,)" should read -- (VIII) --;

Column 22, line 1, in claim 6, "C." should read -- D. --;

lines 17-19, in claim 8, the formula should read:

Column 24, line 12, in claim 25, "(VII,)" should read -- (VIII) --.

Signed and Sealed this

Second Day of May 1978

[SEAL]

Attest:

RUTH C. MASON
Attesting Officer

LUTRELLE F. PARKER
Acting Commissioner of Patents and Trademarks